United States Patent [19]

Thoemel et al.

[11] Patent Number: 4,491,545
[45] Date of Patent: Jan. 1, 1985

[54] PREPARATION OF 2,3,5-TRIMETHYL-P-BENZOQUINONE

[75] Inventors: Frank Thoemel, Weinheim; Werner Hoffmann, Neuhofen, both of Fed. Rep. of Germany

[73] Assignee: BASF Aktiengesellschaft, Ludwigshafen, Fed. Rep. of Germany

[21] Appl. No.: 482,416

[22] Filed: Apr. 6, 1983

[30] Foreign Application Priority Data

Apr. 23, 1982 [DE] Fed. Rep. of Germany ....... 3215095

[51] Int. Cl.$^3$ .............................. C07C 50/04
[52] U.S. Cl. .................................. 260/396 R
[58] Field of Search .............. 260/396 R, 369; 568/747; 252/522 R

[56] References Cited

U.S. PATENT DOCUMENTS

| | | | |
|---|---|---|---|
| 3,663,578 | 5/1972 | Katepow et al. | 260/396 R |
| 3,671,552 | 6/1972 | LeBris et al. | 260/369 |
| 3,700,701 | 10/1972 | Dietl et al. | 260/396 R |
| 3,796,732 | 3/1974 | Brenner | 260/396 R |
| 3,859,365 | 1/1975 | Young | 568/747 |
| 3,956,346 | 5/1976 | Rakoutz | 260/396 R |

FOREIGN PATENT DOCUMENTS

| | | |
|---|---|---|
| 0035635 | 9/1981 | European Pat. Off. |
| 2032081 | 1/1971 | Fed. Rep. of Germany |
| 2450908 | 4/1975 | Fed. Rep. of Germany |
| 2221624 | 5/1979 | Fed. Rep. of Germany |
| 501573 | 2/1971 | Switzerland |

OTHER PUBLICATIONS

Wehrli et al., *J. Org. Chem.*, vol. 37, No. 14, 1972, "Synthesis of Trimethylhydroquinone from Aliphatic Precursors", pp. 2340-2343.

*Primary Examiner*—Glennon H. Hollrah
*Assistant Examiner*—Raymond Covington
*Attorney, Agent, or Firm*—Oblon, Fisher, Spivak, McClelland & Maier

[57] ABSTRACT

Trimethyl-p-benzoquinone of the formula I

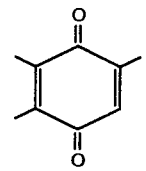

is prepared by a process wherein

A. 2,5,6-trimethylcyclohex-2-en-1-one or 2,3,6-trimethylcyclohex-2-en-1-one is reacted with air or oxygen at from 0° to 150° C. in a virtually anhydrous low molecular weight alkanol in the presence of a catalytic amount of copper(I) oxide or copper(II) oxide and in the presence of from 1 to 10 moles of a hydrogen halide gas per mole of trimethylcyclohexenone, and thereafter B. the reaction mixture, which essentially contains 2,3,6-trimethylphenol and/or 4-halo-2,3,6-trimethylphenol, is mixed with an alkali metal alcoholate in an amount such that a sample, when moistened with water, has a pH of from 3 to 6, and is then reacted with air, pure oxygen or tert.-butyl hydroperoxide at from 0° to 150° C., or wherein from 1 to 10 mole equivalents of a hydrogen halide gas per mole of substrate to be reacted are passed into a mixture containing a virtually anhydrous low molecular weight alkanol and a catalytic amount of copper(I) oxide or copper(II) oxide at from 0° to 30° C., an alkali metal alcoholate is added in an amount such that a sample, when moistened with water, has a pH of from 3 to 6, about one mole equivalent of 2,3,6-trimethylphenol is added and the mixture is then reacted with air, oxygen or tert.-butyl peroxide at from 0° to 150° C.

Trimethyl-p-benzoquinone is an important intermediate for the synthesis of vitamin E.

1 Claim, No Drawings

PREPARATION OF 2,3,5-TRIMETHYL-P-BENZOQUINONE

The present invention relates to a process for the preparation of 2,3,5-trimethyl-p-benzoquinone of the formula I

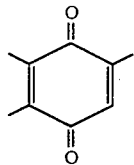

from 2,5,6-trimethylcyclohex-2-en-1-one of the formula II, 2,3,6-trimethylcyclohex-2-en-1-one of the formula III or 2,3,6-trimethylphenol of the formula IV, in each case in a one-pot process.

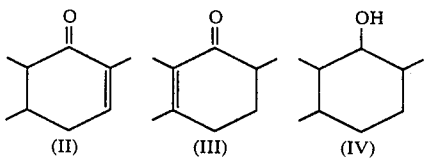

Trimethyl-p-benzoquinone is a direct precursor for the preparation of trimethylhydroquinone, which is an essential intermediate for the preparation of vitamin E. As a result of the constantly increasing demand for vitamin E, there has been no lack of attempts to develop an advantageous method of preparing trimethyl-p-benzoquinone.

P.A. Wehrli et al. [J. Org. Chem. 37 (1972), 2340 and German Laid-Open Application DOS 2,032,081] describe, for example, and indirect electrochemical oxidation of phenol to give benzoquinone. However, this procedure requires special technology.

The oxidation of trimethylphenol with air has been carried out successfully with the aid of cobalt complexes of the "Salcomin" type (cf. German Laid-Open Application DOS No. 2,450,908, Swiss Pat. No. 501,573 and Japanese Pat. No. 7 424 464), but the catalyst required in this procedure is very expensive and has to be prepared beforehand. Furthermore, special solvents (nitriles, dimethylformamide, etc.) are used.

It has also been disclosed that copper salts catalyze the oxidation of alkylphenols with oxygen to give the corresponding quinones. However, German Published Application DOS No. 2,221,624 discloses that this procedure requires uneconomically large amounts of copper salts.

U.S. Pat. No. 3,870,731 and 3,987,068 describe the oxidation with catalytic amounts of copper salts, but the reaction has to be carried out under superatmospheric pressure. As a rule, pure oxygen is used as the oxidizing agent, and this necessitates special safety measures.

As shown in the publications cited above, the starting materials for the synthesis of alkyl-substituted benzoquinones are in general alkyl-substituted phenols. They are obtained, as a rule, by dehydrogenating an alkyl-substituted cyclohexenone, which is a readily available compound, in the presence of a platinum metal catalyst [cf. P.A. Wehrli et al., J. Org. Chem. 37 (1972), 2340].U.S. Pat. No. 3,859,365 describes the oxidation of alkyl-substituted cyclohexenones with air. The catalyst used is copper chloride in the presence of aqueous hydrochloric acid.

Furthermore, European Patent Application No. 0,035,635 discloses a process for the preparation of 2,3,5-trimethyl-p-benzoquinone, wherein 2,5,6-trimethylcyclohex-2-en-1-one is first dehydogenated and the product obtained is then oxidized to trimethyl-p-benzoquinone. Dehydrogenation and oxidation are carried out in the same organic solvent and with the same catalyst, copper (II) halide being used as the latter. The disadvantage of this process is that relatively large amounts of copper salts are required as catalysts, the procedure requiring not less than 1, preferably from 2 to 5, moles of copper salt per mole of starting marterial.

It is an object of the present invention to improve the process for the preparation of 2,3,5-trimethyl-p-benzoquinone, in which 2,5,6-trimethylcyclohex-2-en-1-one is first dehydrogenated and the product obtained is then oxidized, in the same solvent and with the same catalyst, to give trimethyl-p-benzoquinone, and to do this so that a substantially smaller amount of catalyst can be employed.

We have found that this object is achieved by a process for the preparation of trimethyl-p-benzoquinone of the formula I

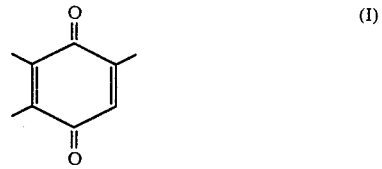

by dehydrogenation of 2,5,6,-trimethylcyclohex-2-en-1-one or 2,3,6-trimethylcyclohex-2-en-1-one in an inert organic solvent in the presence of a copper compound, followed by oxidation of the resulting product in the same inert organic solvent and in the presence of a copper compound, wherein A. 2,5,6-trimethylcyclohex-2-en-1-one or 2,3,6-trimethylcyclohex-2-en-1-one is reacted with air or oxygen at from 0° to 150° C., preferably from 20°to 120° C., in a virtually anhydrous low molecular weight alkanol in the presence of a catalytic amount of copper(I) oxide or copper (II) oxide and in the presence of from 1 to 10 moles of a hydrogen halide gas per mole of trimethylcyclohexenone, and thereafter B. the reaction mixture, which essentially contains 2,3,6-trimethylphenol and/or 4-halo-2,3,6-trimethylphenol, is mixed with an alkali metal alcoholate in an amount such that a sample, when moistened with water, has a pH of from 3 to 6, preferably from 4.0 to 4.4, and is then reacted with air, pure oxygen or tert.-butyl hydroperoxide at from 0° to 150° C., preferably from 20° to 120° C.

We have found that this object is furthermore achieved by a process for the preparation of trimethyl-p-benzoquinone of the formula I, wherein from 1 to 10 mole equivalents of a hydrogen halide gas per mole of substrate to be reacted are passed into a mixture containing a virtually anhydrous low molecular weight alkanol and a catalytic amount of copper(I) oxide or copper (II) oxide at from 0° to 30° C., an alkali metal alcoholate is added in an amount such that a sample, when moistened with water, has a pH of from 3 to 6, preferably from 4.0 to 4.4, in particular about 4.2, about one mole equivalent of 2,3,6-trimethylphenol is added and the mixture is then reacted with air, oxygen or tert.-butyl peroxide at from 0° to 150° C., preferably from 20° to 120° C.

It is surprising that it was possible to find reaction conditions under which 2,5,6-trimethylcyclohex-2-en-1-one or 2,3,6-trimethylcyclohex-2-en-1-one can be converted to the desired 2,5,6-trimethyl-p-benzoquinone in a one-pot reaction, even without employing a molar amount or more of a copper compound, without it being absolutely necessary to use pure oxygen for the dehydrogenation and/or the oxidation, and without having to employ relatively high air and oxygen pressures.

In the reaction according to the invention, air or oxygen is passed into a solution of 2,5,6-trimethylcyclohex-2-en-1-one in a lower alkanol in the presence of a catalytic amount of copper(I) or copper (II) compound and in the presence, at the same time, of a hydrogen halide. By means of gas chromatographic analysis (GCA), it is possible to establish that the subsequent reaction gives first 2,3,6-trimethylcyclohex-2-en-1-one and then 2,3,6-trimethylphenol. After a sufficiently long reaction time, the 2,3,6-trimethylcyclohexen-1-one is completely converted to 2,3,6-trimethylphenol. It an alkali metal alcoholate is then added to the reaction mixture, the amount of the former being such that a sample, when moistened with water, gives a pH of from 3 to 6, preferably about 4.2, and a further amount of air or oxygen is passed in, the phenol is, surprisingly, converted to 2,3,5-trimethyl-p-benzoquinone is good yields. This last-mentioned conversion is surprising insofar as 2,3,6-trimethylphenol in a virtually neutral, or alkaline alcoholic solution in the presence of a catalytic amount of a copper compound cannot be converted to 2,3,5-trimethylbenzoquinone under atmospheric pressure using air or oxygen.

If the reaction mixture comprising 2,5,6-trimethylcyclohex-2-en- 1-one, alkanol, the catalytic amount of copper oxide and hydrogen halide gas, as described above, is allowed to react for a longer time with air or oxygen, 4-halo-2,3,6-trimethylphenol is obtained in addition to 2,3,6-trimethylphenol. If, instead of isolating this product, the reaction mixture is treated, as described above, with an alkali metal alcoholate, and the oxidation with air or oxygen is continued, the 4-halo-2,3,6-trimethylphenol is also converted to 2,3,5-trimethyl-p-benozoquinone. After the reaction products obtained in step A have been treated with an alkali metal alcoholate, they can also be oxidized with tert.-butyl hydroperoxide instead of air or oxygen. Depending on whether trimethylphenol or halotrimethylphenol is the predominant product, subsequent oxidation with tert.-butyl hydroperoxide gives 2,3,5-trimethyl-p-benzoquinone in a yield of from 65 to 80% of theory.

Using the novel catalyst, it is also possible to convert 2,3,6-trimethylphenol to 2,3,5-trimethyl-p-benzoquinone. For this purpose, the catalyst must be prepared beforehand by reaction of a lower alkanol, a hydrogen halide, copper(I) oxide and air, followed by reaction of the product with an alkali metal alcoholate, in the manner described above. The process according to the invention is also simple to carry out technically.

In accordance with the invention, only low molecular weight and virtually anhydrous alkanol, eg. methanol, ethanol, propanol, isopropanol or tert.-butanol, are used as solvents. The amount of solvent employed should be just sufficient to dissolve the substrate to be oxidized. However, care must be taken to ensure that no significant amounts of water are introduced into the reaction mixture, since the oxidation to quinone is unsuccessful in the presence of water.

The reactions according to the invention are carried out in general under atmospheric pressure and at or below the boiling point of the solvent employed, advantageously at from 20° to 100° C., in particular from 40° 80° C. The reaction could in principle also be carried out in a pressure-resistant vessel with air or oxygen being forced in, but employing superatmospheric pressure has no substantial advantages over atmospheric pressure. As a rule, the air or the oxygen is therefore passed into the reaction miture. The amount of air required for oxidation of one mole of substrate is from 10 to 2,000, preferably from 40 to 1,000, liters/hour.

The oxidation of the 2,3,6-trimethylphenol-containing or 4-halo-2,3,6-trimethylphenol-containing reaction mixtures with tert.-butyl hydroperoxide is carried out using a substantially equimolar amount of the peroxide. However, oxidation by air or oxygen to give benzoquinone may also be assisted by the addition of tert.-butyl hydroperoxide. Depending on the particular reaction conditions, it is also possible to manage with less than one mole of tert.-butyl hydroperoxide per mole of substrate to be oxidized. The tert.-butyl hydroperoxide is advantageously added to the stirred reaction mixture at from 35° to 100° C. in the course of from 1 to 4 hours, and the mixture is allowed to continue reacting for about a further two hours.

Depending on the reaction conditions chosen, the reaction time can be from a few hours to a few days.

The alkali metal alcoholate which, according to the invention, has to be added before oxidation of the phenol to benzoquinone must be metered in very precisely. Advantageously, a solution of sodium methylate or sodium ethylate in a lower alkanol, eg. methanol or ethanol is used. The alcoholic solution of the alkali metal alcoholate is added to the stirred reaction mixture, the amount added being such that a sample, when moistened with water, has a pH of from 3 to 6, preferably from 4.0 to 4.4, in particular about 4.2.

The mixture obtained in the reaction according to the invention is worked up in general as follows: it is evaporated down to about ⅓ of its volume by distilling off the solvent, about an equal volume of water is added, the mixture is extracted with an equal amount of toluene, and the extract is washed neutral with water if the pH is not from 5.5 to 7, and is distilled.

Trimethyl-p-benzoquinone is an important intermediate for the preparation of vitamin E.

EXAMPLE 1

55 g of hydrogen chloride were passed into 400 ml of isopropanol at room temperature, and 28 g (0.2 mole) of 2,5,6-trimethylcyclohex-2-en-1-one and 4 g (0.028 mole) of copper(I) oxide were added to the resulting solution. Thereafter, the reaction mixture was heated to 70° C., and 75 liters/hour of air were passed in for 3 hours, while stirring. Gas chromatographic analysis (2 m OV 17, 200° C.) then showed that 2,5,6-trimethylcyclohex-2-en-1-one was no longer present, and that 2,3,6-trimethylphenol as well as a little 4-chloro-2,3,6-trimethylphenol had beed formed. 243 ml of a 30% strength solution of sodium methylate in methanol were then run in at room temperature, and a sample of the reaction mixture, after water had been added to it, had a pH of 4.2. The mixture was then heated at 62° C., and 75 liters/hour of air, which had been fed in uninterrupted throughout the entire process, was passed into the mixture at 62° C. for a further 16 hours.

Working up was carried out as follows: the solvent was substantially distilled off, the residue was poured onto about an equal volume of water, the mixture was extracted with 200 ml of toluene, the extract was washed with water, the organic phase was evaporated down in a rotary evaporator, and the residue was distilled over a Claisen bridge to give 21.9 g of product at from 61 to 115° C./0.1 mbar. According to gas chromatographic analysis (GCA), this product contained 85% of 2,3,5-trimethyl-p-benzoquinone and 10% or 4-chloro-2,3,6-trimethylphenol. The yeild of 2,3,5-trimethyl-p-benzoquinone was thus 62% of theory.

EXAMPLE 2

45 g of hydrogen chloride were passed into 400 ml of isopropanol at room temperature, 4 g (0.028 mole) of $Cu_2O$ and 28 g (0.2 mole) of 2,5,6-trimethylcyclohex-2-en-1-one were added to the resulting solution, the entire mixture was heated at 70° C., and 75 liters/hour of air was passed in for 2 hours at 70° C., while stirring. GCA then showed that all of the trimethylcycohexenone had been converted to trimethylphenol. Thereafter, 180 ml of a 30% strength solution of $NaOCH_3$ in $CH_3OH$ were added to the reaction mixture (a sample then had a pH of 4.2 after water had been added), the mixture was heated at 40° C., 28 g (0.3 mole) of tert.-butyl hydroperoxide were added in the course of 2 hours, while stirring, and, finally, stirring was continued for a further 2 hours at 40° C.

Working up was carried out as follows: the solvent was substantially distilled off, the residue was poured onto an equal volume of water, the mixture was extracted with 900 ml of toluene, the extract was washed with water, the organic phase was evaporated down in a rotary evaporator, and the residue was distilled over a Claisen bridge to give 21.4 g of product. According to GCA, this product contained 89.5% of 2,3,5-trimethyl-p-benzoquinone. The yield was thus 64% of theory.

EXAMPLE 3

52 g of HCL gas were passed into 400 ml of isopropanol at room temperature, 4 g (0.028 mole) of $Cu_2O$ and 28 g (0.2 mole) of 2,5,6-trimethylcyclohex-2-en-1-one were added to the resulting solution, the entire mixture was heated 70° C. and 75 liters/hour of air were passed in for 14 hours, while stirring. GCA showed that the reaction mixture then contained 94% of 4-chloro-2,3,6-trimethylphenol as well as 4% of 2,3,6-trimethylphenol. Thereafter, 150 ml of a 30% strength solution of $NaOCH_3$ in $CH_3OH$ were added to the reaction mixture at from 10° to 20° C. (a sample then had a pH of 4.2 after water had been added), the mixture was heated at 40° C., 19 g (0.2 mole) of tert.-butyl hydroperoxide were added in the course of 2 hours at 40° C., while stirring, and stirring was continued for a further 7 hours at 40° C. GCA then showed that 75% of the 4-chlorotrimethylphenol present had been converted. Thereafter, a further 10 g (0.1 mole) of tert.-butyl hydroperoxide were added in the course of 1 hour at 40° C., and the reaction mixture was stirred for a further 3 hours at 40° C. The mixture was worked up as described in Example 1 to give 25.2 g of product. According to GCA, this product contained 95% of 2,3,5-trimethyl-p-benzoquinone. The yield was thus 80% of theory.

EXAMPLE 4

53 of HCL gas were passed into 400 ml of isopropanol at room temperature, 4 g (0.028 mole) of $Cu_2O$ were added to the resulting solution, the mixture was stirred for 5 minutes and 300 ml of a 30% strength solution of $NaOCH_3$ in $CH_3OH$ were then added at from 10° to 20° C. (a sample had a pH of 4.2 after water had been added). 28 g (0.2 mole) of 2,3,6-trimethylphenol were then added rapidly to the resulting reaction mixture, the mixture was heated to 60° C. and 75 liters/hour of air were passed in for 21 hours. According to GCA, the trimethylphenol had then been completely converted to 2,3,5-trimethyl-p-benzoquinone.

The mixture was worked up as described in Example 1 to give 21.74 g of product, which contained 99.5% of 2,3,5-trimethyl-p-benzoquinone. The yield was thus 72% of theory.

EXAMPLE 5

10 g of HCL gas were passed into 400 ml of isopropanol at room temperature, 4 g (0.028 mole) of $Cu_2O$ were added to the resulting solution, the mixture was heated at 70° C. and 75 liters/hour of air were passed in for 4 hours. Thereafter, 24 ml of a 30% strength solution of $NaOCH_3$ in $CH_3OH$ were added at room temperature (a sample has a pH of 4.2 after water had been added), followed by the addition of 28 g (0.2 mole) of 2,3,6-trimethylphenol, the mixture was heated at 40° C. and 18 g (0.2 mole) of tert.-butyl hydroperoxide were then added in the course of 2 hours. At the same time, 75 liters/hour of air were passed into the reaction mixture. After a reaction time of 12 hours, the mixture was worked up as described in Example 1 to give 22.54 g of 99.7% pure 2,3,5-trimethyl-p-benzoquinone. The yield was thus 76% of theory.

We claim:

1. A process for the preparation of trimethyl-p-benzoquinone of the formula I

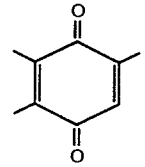

which comprises dehydrogenating 2,5,6-trimetylcyclohex-2-en-1-one or 2,3,6-trimethylcyclohex-2-en-1-one in an inert organic solvent in the presence of a copper compound, then oxidizing the resulting product in the same inert organic solvent and in the presence of a copper compund, wherein said 2,5,6-trimethylcyclohex-2-en-1-one or 2,3,6-trimethylcyclohex-2-en-1-one is reacted with air or oxygen at from 0° to 150° C. in a substantially anhydrous low molecular weight alkanol in the presence of a catalytic amount of copper (I) oxide or copper (II) oxide and in the presence of from 1 to 10 moles of a hydrogen halide gas per mole of trimethylcyclohexenone, and said reaction mixture, which essentially contains 2,3,6-trimethylphenol or 4-halo-2,3,6-trimethylphenol, or a mixture thereof, is mixed with an alkali metal alcoholate in an amount such that a sample, when moistened with water, has a pH of from 4.0 to 4.4, and is then reacted with air, pure oxygen or tert-butyl hydroperoxide at from 0° to 150° C.

* * * * *